Figure 1:
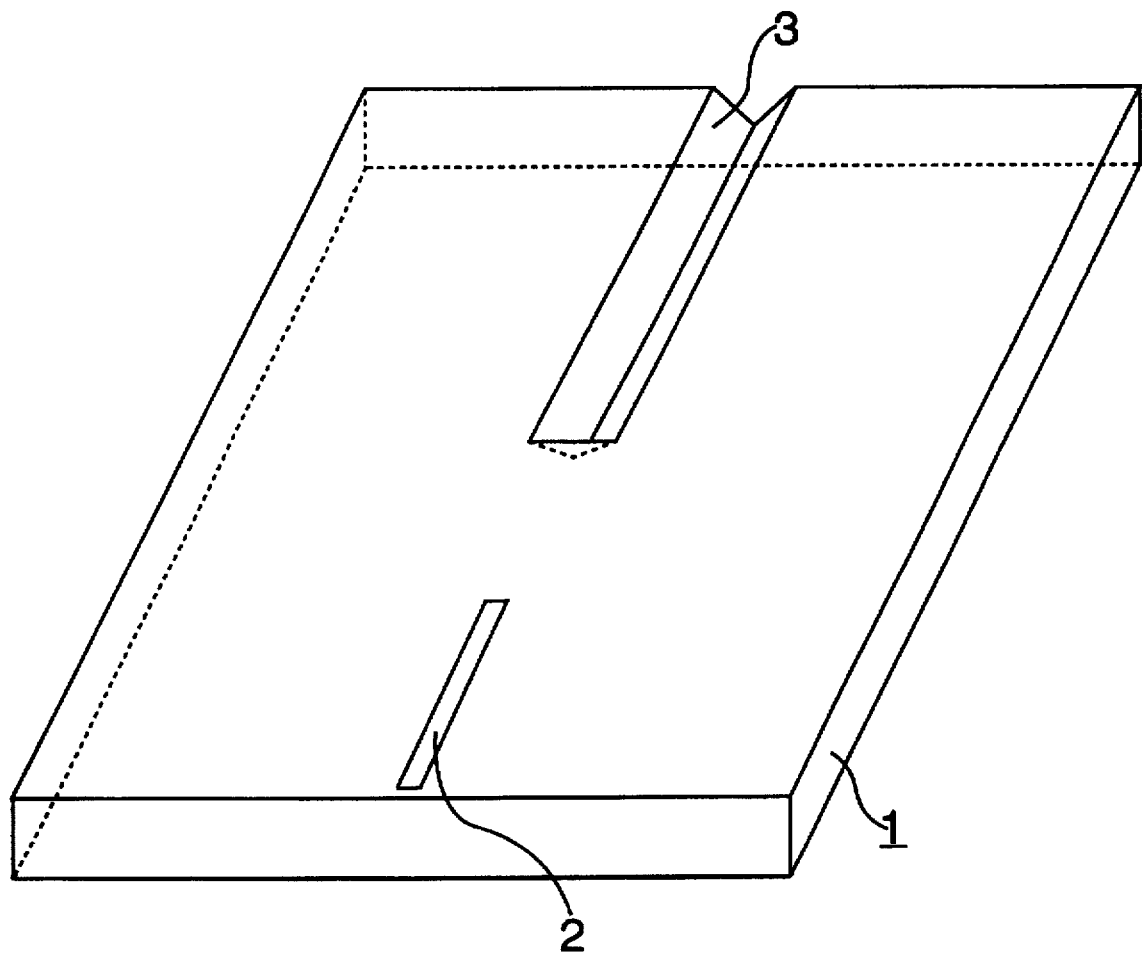

United States Patent [19]

Splett

[11] Patent Number: 5,700,382

[45] Date of Patent: Dec. 23, 1997

[54] METHOD FOR FABRICATING A SILICON SEMICONDUCTOR SUBSTRATE HAVING AN INTEGRATED WAVEGUIDE AND AN OPTICAL FIBER COUPLED THERETO

[75] Inventor: Armin Splett, München, Germany

[73] Assignee: Siemens Aktiengesellschaft, München, Germany

[21] Appl. No.: 591,619

[22] PCT Filed: Jul. 15, 1994

[86] PCT No.: PCT/DE94/00867

§ 371 Date: Apr. 1, 1996

§ 102(e) Date: Apr. 1, 1996

[87] PCT Pub. No.: WO95/04296

PCT Pub. Date: Feb. 9, 1995

[30] Foreign Application Priority Data

Jul. 27, 1993 [DE] Germany ............................ 4325955.3

[51] Int. Cl.⁶ .............................. H01L 21/00; B44C 1/22
[52] U.S. Cl. .................... 216/24; 156/633.1; 156/645.1; 156/657.11; 216/2; 216/33; 216/41; 216/52
[58] Field of Search .................. 156/633.1, 645.1, 156/647.1, 657.1, 659.11; 216/2, 24, 33, 41, 52; 385/15, 52, 80, 83

[56] References Cited

U.S. PATENT DOCUMENTS

| | | | |
|---|---|---|---|
| 5,017,263 | 5/1991 | Clark | 156/647.1 X |
| 5,466,558 | 11/1995 | Sasaki | 156/647.1 X |

FOREIGN PATENT DOCUMENTS

| | | |
|---|---|---|
| 0 361 153 | 4/1990 | European Pat. Off. |
| 41 33 150 | 4/1993 | Germany. |
| 41 42 850 | 6/1993 | Germany. |
| 59-197184 | 11/1984 | Japan. |

OTHER PUBLICATIONS

Grant, et al. "Low–loss Coupling of Ribbon Fibres to Silica–on Silicon Integrated Optics Using Preferentially Etched V–grooves", Integrated Photonics Research, 1991, pp. 166–167.

Primary Examiner—William Powell
Attorney, Agent, or Firm—Kenyon & Kenyon

[57] ABSTRACT

A method for fabricating a silicon semiconductor substrate having an optical fiber coupled to an integrated waveguide by anisotropically etching a V-shaped groove aligned with the integrated waveguide into the substrate. The integrated waveguide is provided with a freely accessible end surface situated opposite the end of the V-shaped groove. The freely accessible end surface is formed by first producing a recess in the silicon semiconductor substrate. The recess is made by anisotropically etching a piece of the substrate from the surface opposite the surface bearing said V-shaped groove. The piece is bared down to a region surrounding said integrated waveguide but the piece remains connected to the waveguide by a V-shaped notch. Then pressure is exerted on the piece, causing it to break off at the V-shaped notch, thus forming the freely accessible end surface of the waveguide as a fracture surface. An optical fiber is inserted into the V-shaped groove and extended up to the freely accessible end surface.

4 Claims, 4 Drawing Sheets

METHOD FOR FABRICATING A SILICON SEMICONDUCTOR SUBSTRATE HAVING AN INTEGRATED WAVEGUIDE AND AN OPTICAL FIBER COUPLED THERETO

The invention relates to a method for fabricating a silicon semiconductor substrate having an integrated waveguide and an optical fiber coupled thereto, in the case of which the integrated waveguide is provided with a freely accessible end surface by producing a recess in the silicon semiconductor substrate, the end surface at the recess is situated opposite the end of a V-shaped groove etched anisotropically in the silicon semiconductor substrate, and the optical fiber is inserted into the groove, extending up to the freely accessible end surface of the integrated waveguide.

It is known from an essay by M. F. Grant, S.Day and R. Bellerby, "Low-loss coupling of ribbon fibres to silica-on-silicon integrated optics using preferentially etched V-grooves" in "Integrated Photonics Research", (Summaries of papers presented at the Integrated Photonics Research Topical Meeting, Apr. 13–16, 1992, New Orleans—Technical Digest Series, vol. 10, pp. 166–167) to produce a semiconductor substrate with an integrated waveguide and an optical fiber coupled thereto by first introducing a V-shaped groove into the semiconductor substrate through anisotropic etching. Waveguide layers are then applied to the semiconductor substrate. A duct-type waveguide is subsequently formed through a reactive ion etching. The semiconductor substrate prepared thus far is subsequently provided with a groove by means of sawing in the manner that a perpendicularly running end surface of the integrated waveguide is produced so as to be freely accessible. After that, the optical fiber is inserted into the V-shaped groove so as to extend up to the freely accessible end surface of the integrated waveguide. In this manner, one obtains a silicon semiconductor substrate with an integrated waveguide and an optical fiber coupled thereto, where the optical fiber is aligned to the freely accessible end surface of the integrated waveguide, provided that the saw cut is executed with a comparable exact alignment.

The object of the invention is to propose a method for fabricating a silicon semiconductor substrate with an integrated semiconductor and an optical fiber coupled thereto, which will make it possible to produce a silicon semiconductor substrate that is distinguished by a very high optical quality of the coupling site, cost-effectively, and with a very precise alignment of the optical fibers to the freely accessible end surface of the integrated waveguide.

As a means for achieving this objective as in a method of the type indicated at the outset, the invention proposes forming the recess in the silicon semiconductor substrate by separating out a piece of the silicon semiconductor substrate by baring the piece to be cut right down to a region surrounding the integrated waveguide by means of anisotropic etching from the surface of the silicon semiconductor substrate opposite the surface bearing the groove, the region surrounding the integrated waveguide being weakened by the etching of a V-shaped notch; pressure is exerted on the piece to be separated out, causing it to subsequently break off at the V-shaped notch, while the freely accessible end surface of the integrated waveguide is formed as a fracture surface.

It is, in fact, disclosed by the German Provisional Patent 41 42 850 A1 in a semiconductor substrate having an integrated waveguide in the region of the coupling site to provide a recess in the form of an etch pit between the waveguide and the optical fiber by means of depth etching, however, the semiconductor substrate is made of a III–V semiconductor material, and the semiconductor substrate is composed of a plurality of layers comprising, inter alia, an etch layer that enables a selective wet etching. This etch layer is laid bare by the etch pit, so that a portion of the etch layer can be dissolved out by means of selective wet etching in the vicinity of the etch pit. The portion of the etch layer that is dissolved out lies under a ridge [land or stepped feature] with a tab [tongue] that was left standing during the depth etching. The ridge and tab are thus laid bare, so that the tab can be broken off by means of ultrasound while forming a low-loss, optical butting coupling.

The essential advantage of the method according to the invention over the method described by the Grant essay discussed at the outset consists in that by means of the anisotropic etching, the piece to be separated out and also the V-shaped notch are able to be exactly fixed in their position relatively to one another and to the V-shaped groove, thus enabling a very precise alignment of the optical fiber to the freely accessible end surface of the integrated waveguide. Another important advantage is that the freely accessible end surface of the integrated waveguide produced by the fracture surface forms a coupling surface distinguished by a very high surface quality, which leads to a further increase in the optical quality of the coupling. A comparison to the method that is inferable from the above described German Provisional Patent 41 42 850 A1 reveals the advantage that one can do without a semiconductor substrate having a multilayer structure; moreover, one only needs to implement one anisotropic etching method.

When working with the method as set forth by the invention, it is viewed as advantageous when a mask is applied to the surface of the semiconductor substrate opposing the surface bearing the groove to separate out the piece of the semiconductor substrate, in the region of the freely accessible end surface to be formed of the integrated waveguide, this mask having a strip which is accessible to the anisotropically acting etching medium and which has dimensions which enable the V-shaped notch to be formed during etching. The special advantage of this embodiment of the method according to the invention consists in that to separate the piece out of the semiconductor substrate, a single mask can be applied in a photolithographic process to the surface of the semiconductor substrate opposing the surface bearing the groove; as a result, the entire fabrication method turns out to be cost-effective. An additional advantage is seen in that the size of the fracture surface is able to be established by the mask or the strip, because the dimensions of the strip accessible to the etching medium in the area of the integrated waveguide are proportioned to conform with the thickness of the semiconductor substrate.

In another advantageous specific embodiment of the method according to the invention, pressure is exerted in the manner that the semiconductor substrate receives an oncoming flow of a liquid or a gas. This results, inter alia, in the advantageous possibility of inexpensively producing semiconductor substrates still in the wafer composite in accordance with the method of the invention.

To elucidate the invention, FIGS. 1 through 4 illustrate a specific embodiment of the method according to the invention on the basis of various depicted fabrication states of a semiconductor substrate having an integrated waveguide and an optical fiber coupled thereto.

FIG. 1 shows a semiconductor substrate 1, which is already provided with an integrated optical waveguide 2 and a V-shaped groove 3; the semiconductor substrate can be manufactured in this case as was described at the outset in the clarification of the known method.

In one fabrication state as shown in FIG. 1, the semiconductor substrate 1 is subsequently provided photolithographically with a mask 4 (compare FIG. 2) on a surface 5 which lies opposite the surface 6 bearing the V-shaped groove 3. The mask 4 is so shaped that, in one region 7 below the end 8 of the integrated waveguide 2, it covers a surface that is not accessible to the anisotropically acting etching medium. Bordering on edges 9, 10 and 11 of the region 7 are relatively broadly designed exposed surfaces 12, 13 and 14, which with regard to the action of the anisotropically functioning etching medium are so dimensioned that, during etching, a piece 15 of the semiconductor substrate 1 to be cut (compare FIG. 3) is laid bare except for a region 16 surrounding the waveguide 2. It is, namely, the aim in this region 16 to merely form a V-shaped notch 17, which is why the mask 4 leaves exposed a strip 18 that is accessible to the anisotropically functioning etching medium. With regard to the V-shaped notch 17 that forms during anisotropic etching, this strip 18 is so selected that the notch on no account reaches into the region of the integrated waveguide 2, but rather, viewed from the surface 6, ends below the integrated waveguide 2.

Figure 2:
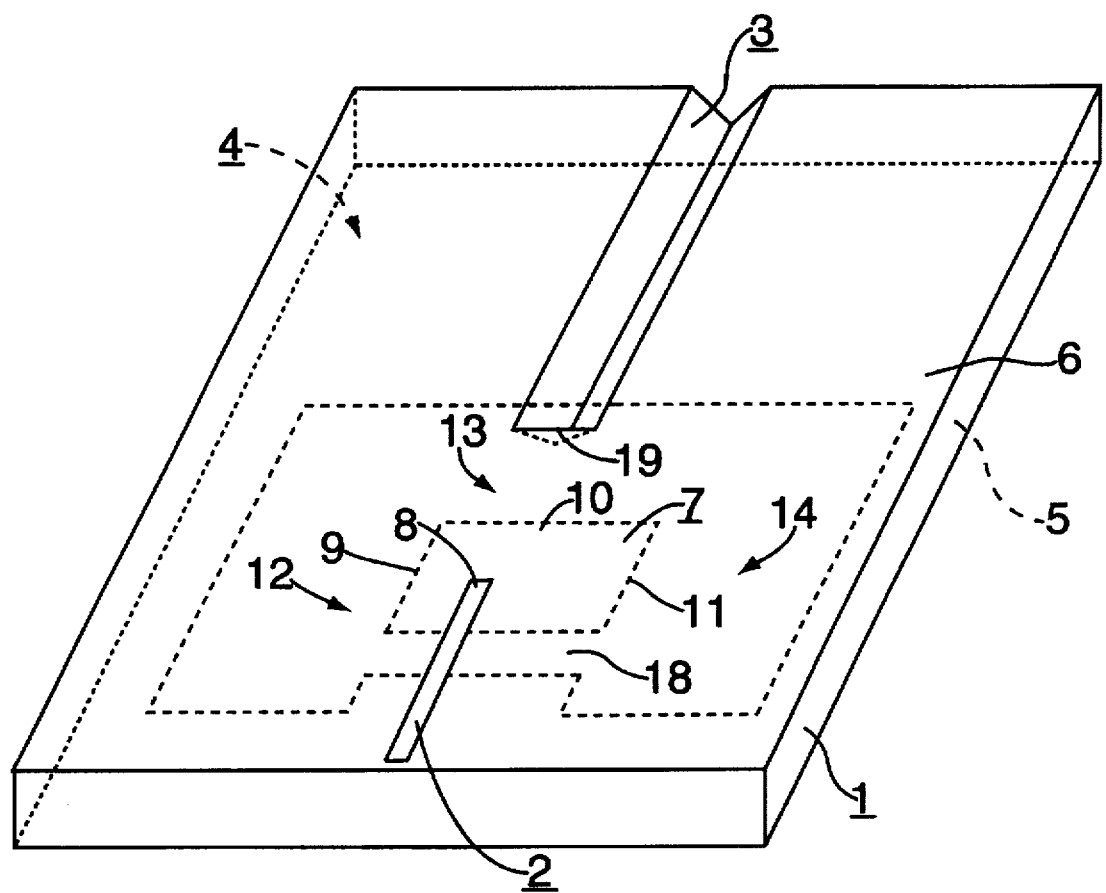
Figure 3:
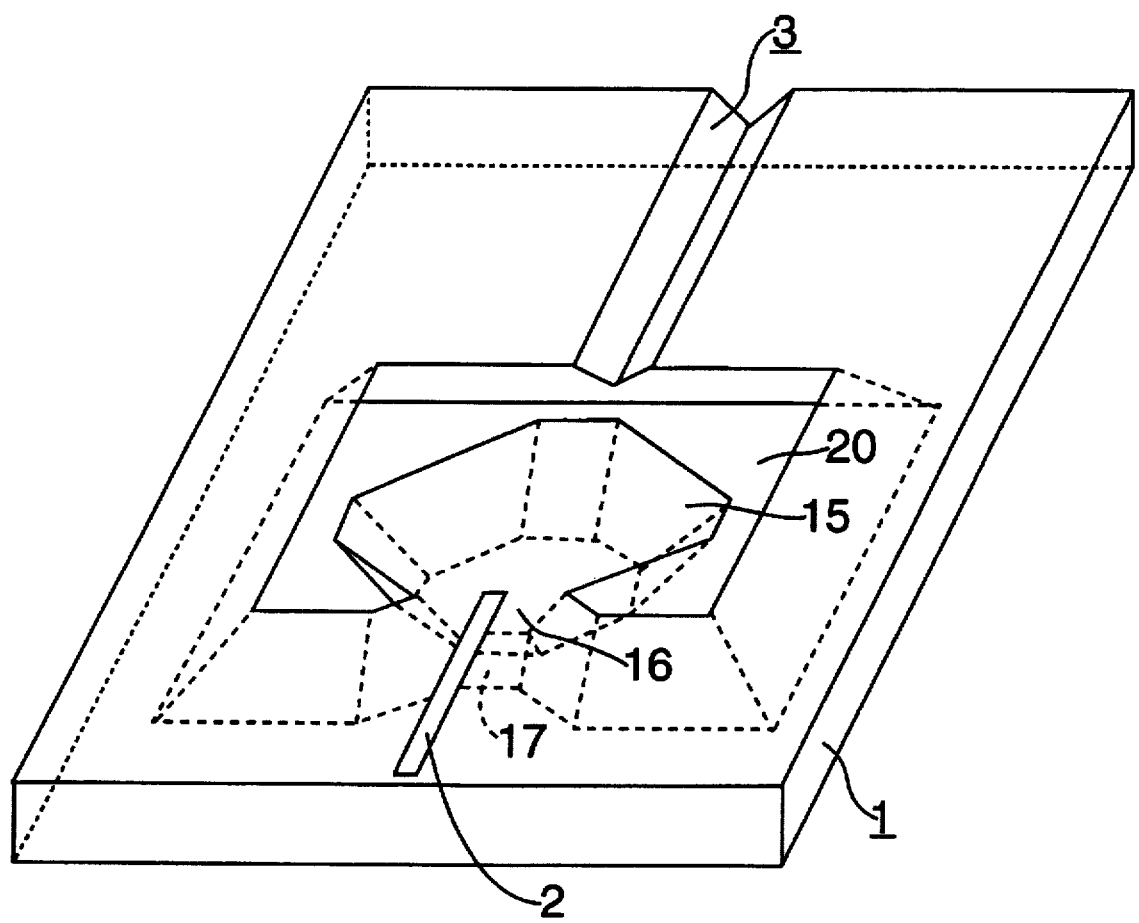

The semiconductor substrate 1 provided with the described mask as shown in FIG. 2 is subsequently etched anisotropically, forming a configuration, as depicted in FIG. 3. This Figure clearly reveals that the piece 15 to be separated out is only still joined to the semiconductor substrate 1 at the side of a recess 20 already partially formed thus far, opposite the end 19 of the V-shaped groove 3. If the semiconductor substrate 1 subsequently receives an oncoming flow of a liquid or a gas in the embodiment of FIG. 3 and, as a result, a pressure is exerted on the thus far bared piece 15 to be cut, then this piece breaks off in the area of the V-shaped notch 17. A fracture surface 21 aligned in a direction normal to the V-shaped groove 3 (see FIG. 4) of high optical quality is thereby formed, in which the integrated waveguide 2 terminates while forming a freely accessible end surface 22. Further details regarding the optical quality of such a fracture surface can be gleaned from the German Provisional Patent 41 33 150 A1.

Figure 4:
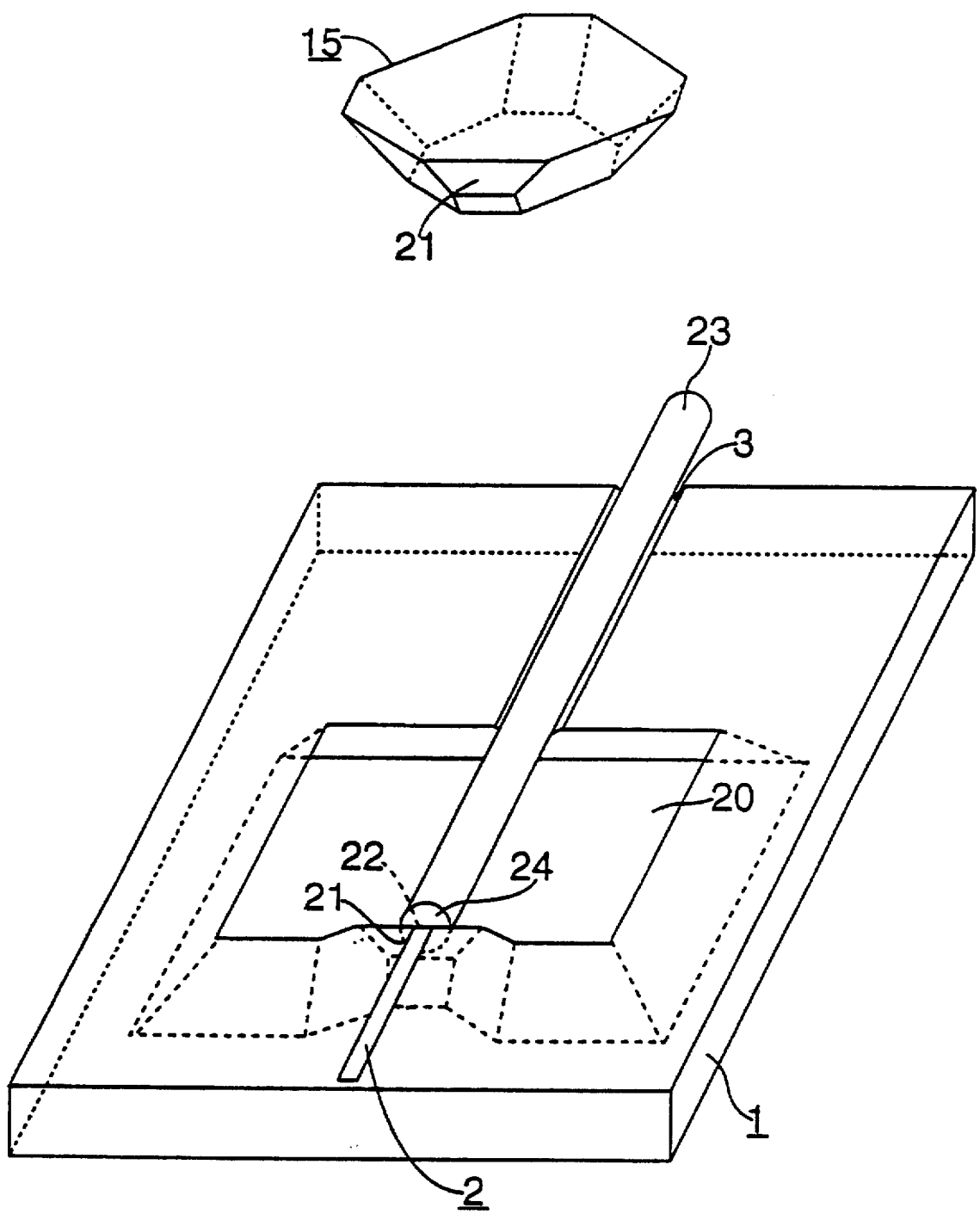

To better illustrate this, FIG. 4 shows, at the bottom, the semiconductor substrate 1 with the now completed recess 20 and, at the top, the piece 15 separated out. Shown with dotted lines on the piece 15 is the fracture surface 21, which is hidden in the bottom representation of FIG. 4.

In addition, FIG. 4 reveals that an optical fiber 23 is inserted into the V-shaped groove 3 and, in fact, so that it extends with its front side 24 up to the freely accessible end surface 22 of the integrated waveguide 2 or up to the fracture surface 21.

I claim:

1. A method for fabricating a silicon semiconductor substrate having an integrated waveguide and an optical fiber coupled thereto, comprising the steps of:

a) providing an integrated waveguide in a silicon semiconductor substrate;

b) anisotropically etching a V-shaped groove into said silicon semiconductor substrate aligned with said waveguide;

c) providing said integrated waveguide with a freely accessible end surface situated opposite the end of the V-shaped groove by producing a recess in the silicon semiconductor substrate, the formation of said recess comprising the steps of:

1) anisotropically etching a piece of the semiconductor substrate from the surface of said silicon semiconductor substrate opposite the surface beating said V-shaped groove, wherein said piece is bared down to a region surrounding said integrated waveguide, and wherein said piece remains connected to said waveguide by a V-shaped notch;

2) exerting pressure on said piece, causing it to break off at said V-shaped notch, forming said freely accessible end surface of said integrated waveguide as a fracture surface;

d) inserting an optical fiber into the V-shaped groove, said optical fiber extending up to said freely accessible end surface.

2. The method of claim 1, wherein a mask is applied to the surface of said silicon semiconductor substrate opposite the surface bearing said V-shaped groove, said mask being used to separate out said piece of said silicon semiconductor substrate thereby forming said recess, said mask having a strip that is accessible to anisotropically acting etching medium in the region in which said freely accessible end surface is to be formed, said strip being shaped to enable said V-shaped notch to be formed during etching.

3. The method of claim 1, wherein pressure is applied to said semiconductor substrate to separate said piece to form said recess by applying an oncoming flow of a liquid or a gas.

4. The method of claim 2, wherein pressure is applied to said semiconductor substrate to separate said piece to form said recess by applying an oncoming flow of a liquid or a gas.

* * * * *